United States Patent
Sato et al.

(10) Patent No.: US 10,485,419 B2
(45) Date of Patent: Nov. 26, 2019

(54) OPTICAL IMAGING APPARATUS AND METHOD FOR CONTROLLING THE SAME

(71) Applicant: CANON KABUSHIKI KAISHA, Tokyo (JP)

(72) Inventors: Toshiaki Sato, Kawasaki (JP); Futoshi Hirose, Yokohama (JP); Kohei Takeno, Yokohama (JP); Kaishi Ohashi, Tokyo (JP); Kei Suzuki, Chigasaki (JP); Shoichi Yamazaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 63 days.

(21) Appl. No.: 15/326,436

(22) PCT Filed: Jun. 30, 2015

(86) PCT No.: PCT/JP2015/003297
§ 371 (c)(1),
(2) Date: Jan. 13, 2017

(87) PCT Pub. No.: WO2016/009603
PCT Pub. Date: Jan. 21, 2016

(65) Prior Publication Data
US 2017/0196450 A1   Jul. 13, 2017

(30) Foreign Application Priority Data

Jul. 16, 2014 (JP) ................................. 2014-145915
Apr. 9, 2015 (JP) ................................. 2015-080445

(51) Int. Cl.
*A61B 3/12* (2006.01)
*A61B 3/10* (2006.01)
(Continued)

(52) U.S. Cl.
CPC .......... *A61B 3/1025* (2013.01); *A61B 3/0025* (2013.01); *A61B 3/0058* (2013.01); *A61B 3/12* (2013.01); *A61B 5/0068* (2013.01)

(58) Field of Classification Search
CPC ... A61B 3/1025; A61B 3/0025; A61B 3/0058; A61B 3/12; A61B 5/0068
(Continued)

(56) References Cited

U.S. PATENT DOCUMENTS 7,311,771 B2 * 12/2007 Taniguchi .......... B23K 26/0613
117/4
2011/0237895 A1 * 9/2011 Yoshida ............. A61B 1/00009
600/180

(Continued)

FOREIGN PATENT DOCUMENTS

EP        2630908 A1   8/2013
JP    2009-95632 A     5/2009

OTHER PUBLICATIONS

Sulai, Y.N., et al, "Visualization of retinal vascular structure and perfusion with a nonconfocal adaptive optics scanning light ophthalmoscope", J. Opt. Soc. Am. A., Mar. 2014, pp. 569-579, vol. 31, No. 3.

*Primary Examiner* — James R Greece
(74) *Attorney, Agent, or Firm* — Canon U.S.A., Inc., IP Division

(57) ABSTRACT

An optical imaging apparatus includes a splitting unit configured to split return light, obtained by applying measurement light from a light source to an object to be examined via a measurement optical path, into a plurality of beams, a light receiving unit configured to measure intensities of the beams, a changing unit configured to change a ratio of signal components of as an image to be displayed based on the measured intensities of the beams, an angle specifying unit configured to specify an angle, and a generating unit con-
(Continued)

figured to generate an image by calculation using the changed ratio of the signal components. The ratio of signal components of an image to be displayed based on intensities of beams is changed in accordance with information about a specified angle to generate an image of an object such that the direction of edge enhancement on the object is changed.

16 Claims, 11 Drawing Sheets

(51) Int. Cl.
    *A61B 5/00*     (2006.01)
    *A61B 3/00*     (2006.01)

(58) Field of Classification Search
    USPC .......................................... 351/205, 206, 246
    See application file for complete search history.

(56) References Cited

U.S. PATENT DOCUMENTS

| | | |
|---|---|---|
| 2011/0273668 A1 | 11/2011 | Hirose |
| 2012/0075640 A1* | 3/2012 | Sakagawa .............. A61B 3/102 356/511 |

* cited by examiner

[Fig. 1A]
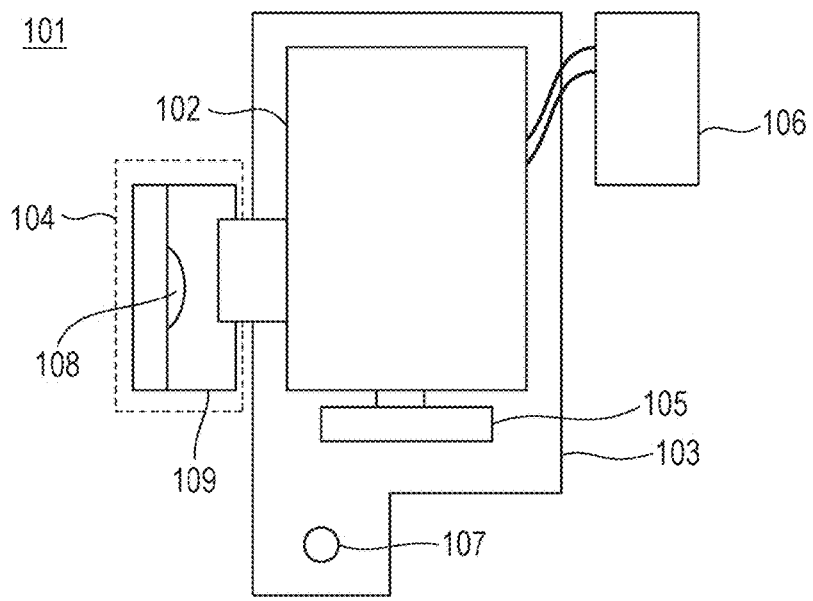
[Fig. 1B]
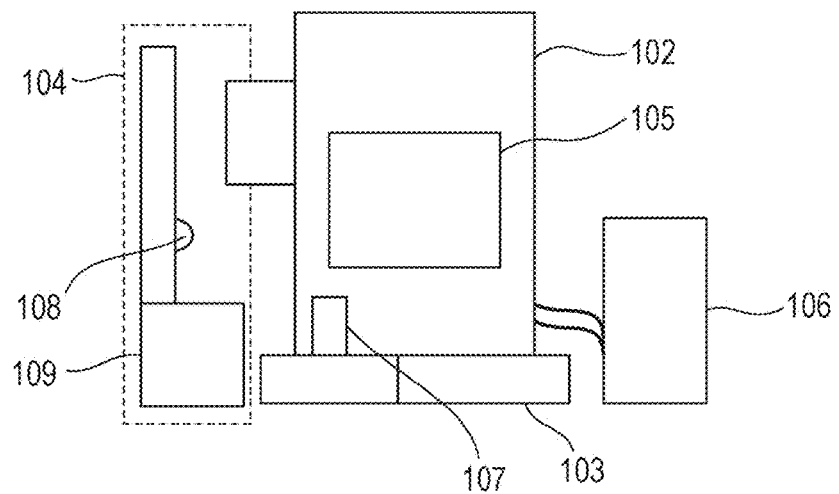

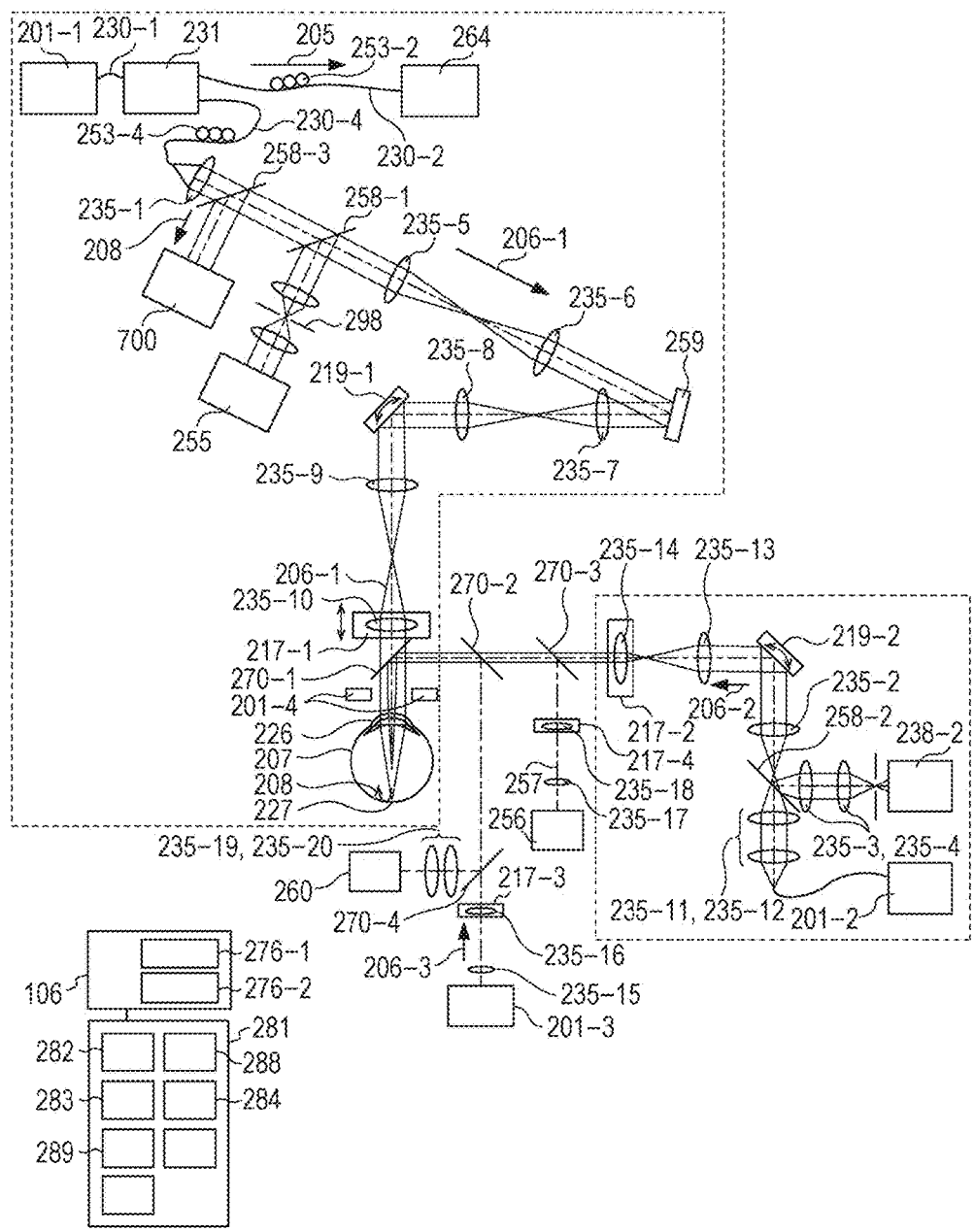
[Fig. 2A]

[Fig. 2B]
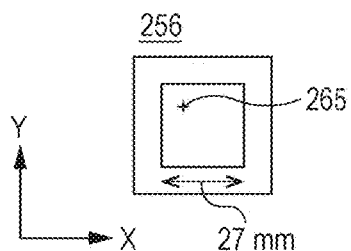
[Fig. 3]
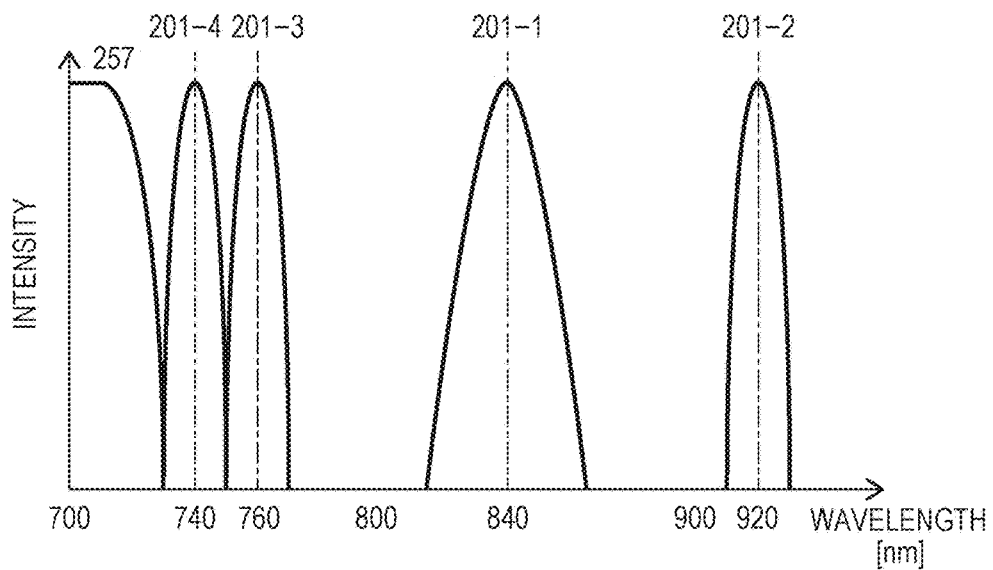

[Fig. 4]
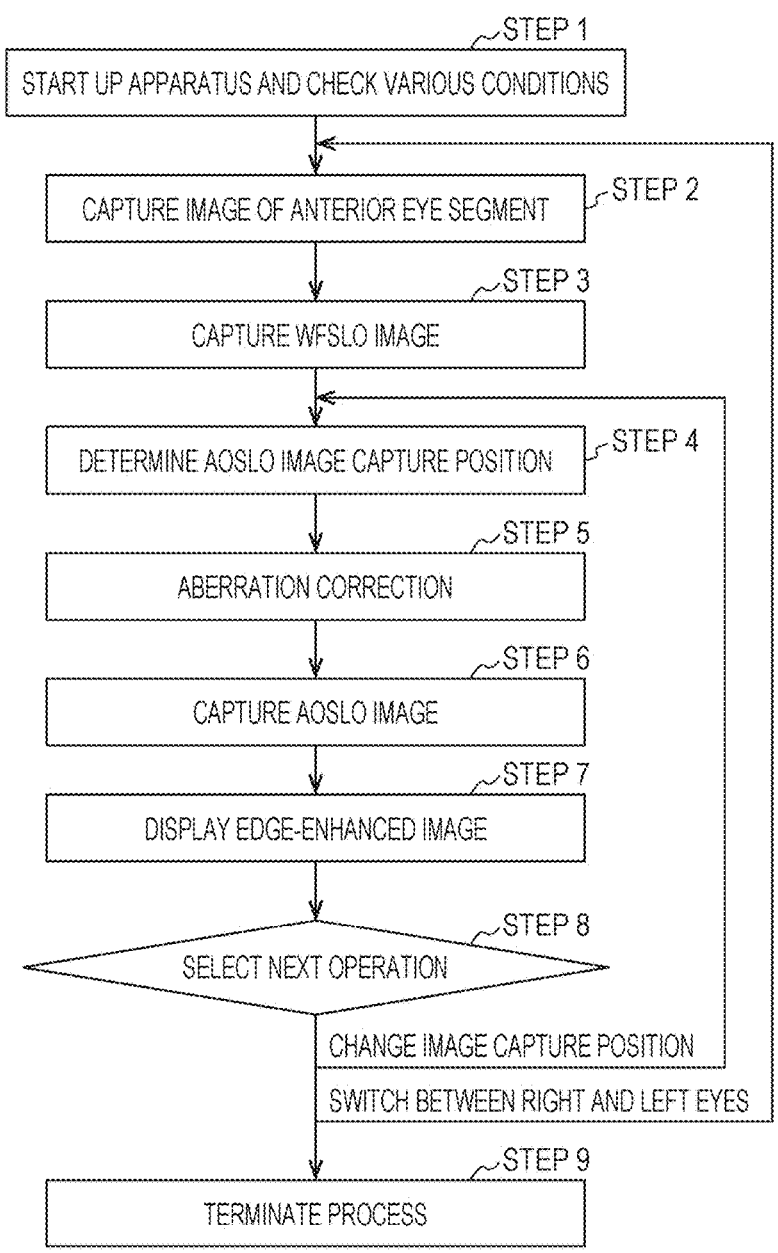

[Fig. 5]
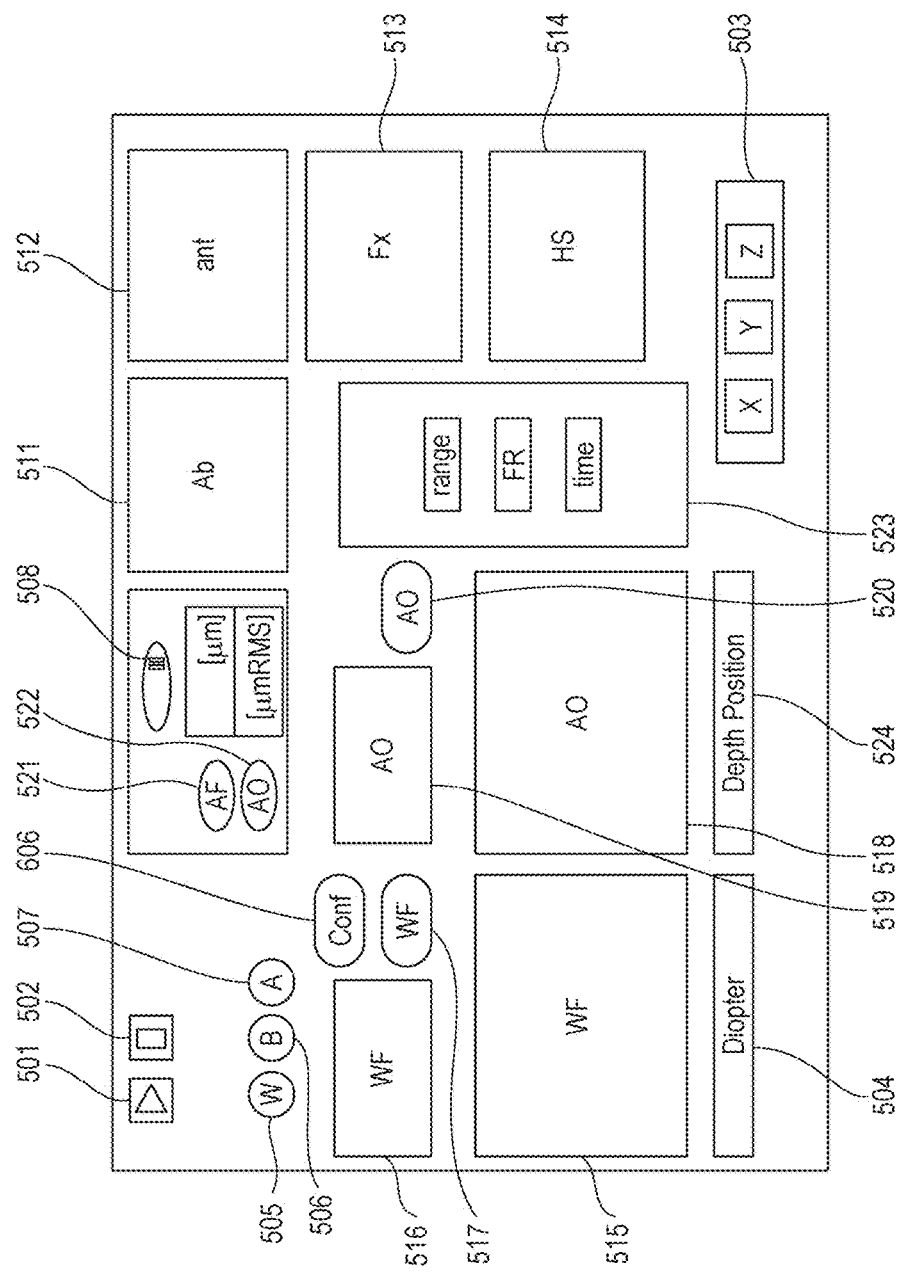

[Fig. 6]
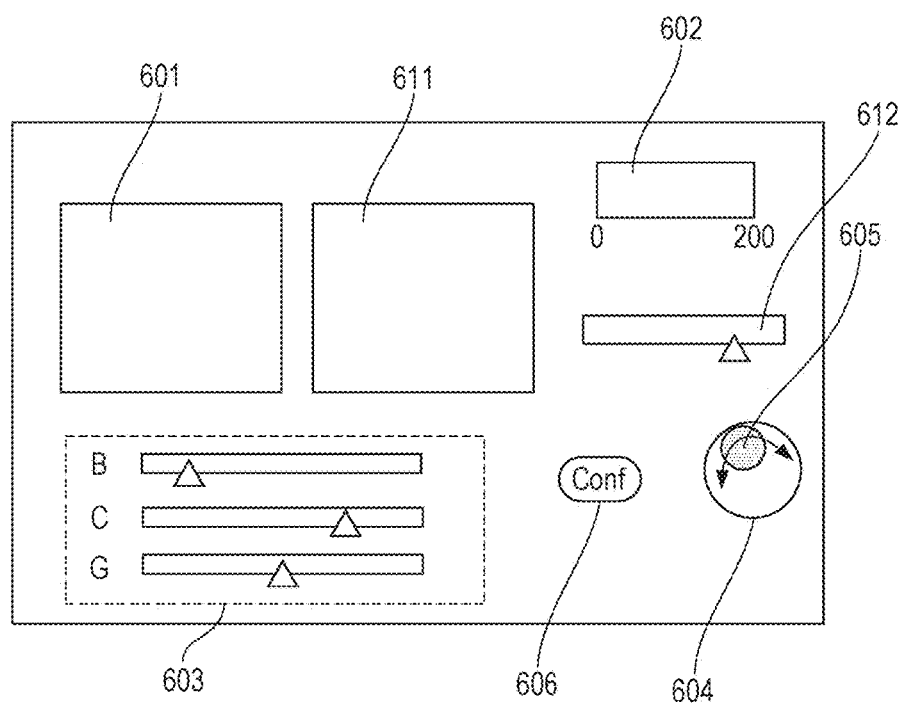
[Fig. 7A]
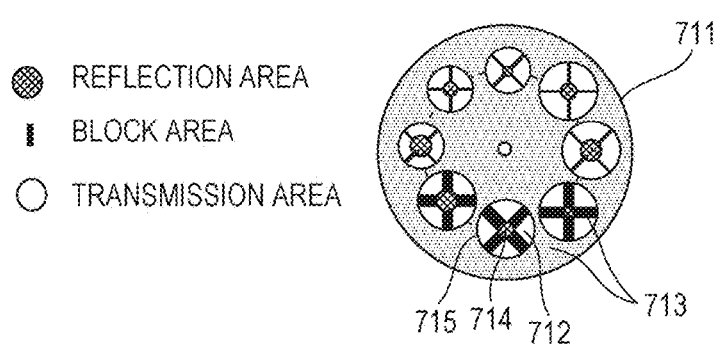
- REFLECTION AREA
- BLOCK AREA
- TRANSMISSION AREA

[Fig. 7B]
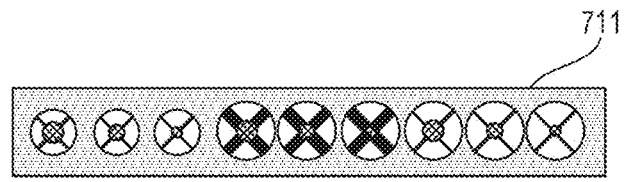
[Fig. 8]
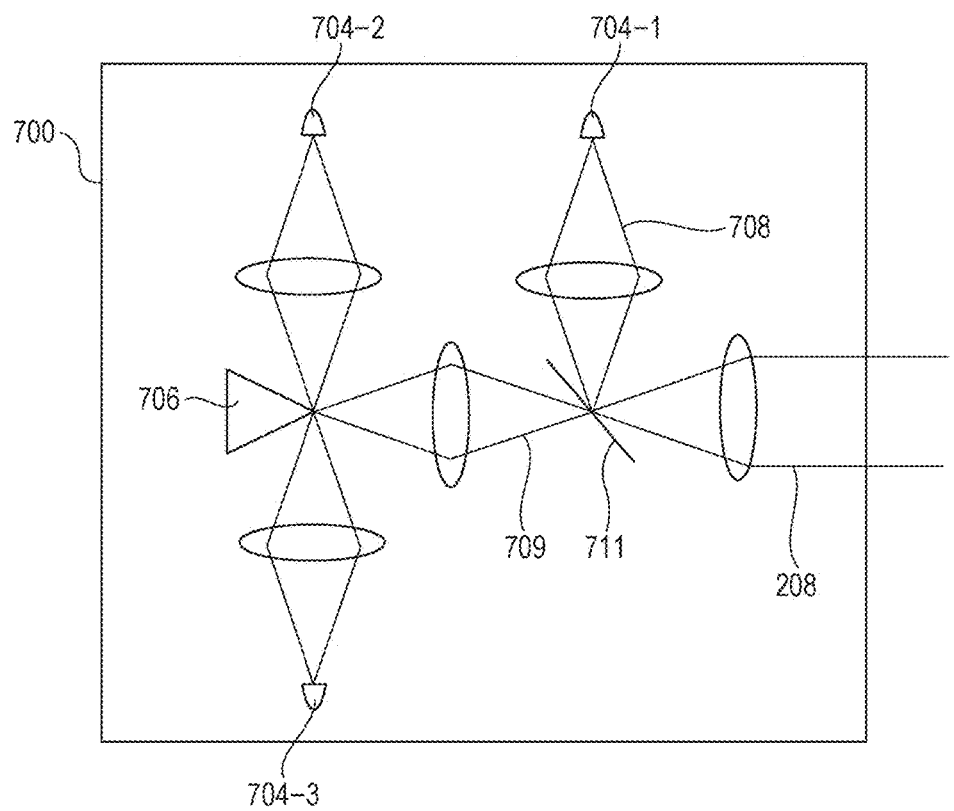

[Fig. 9]
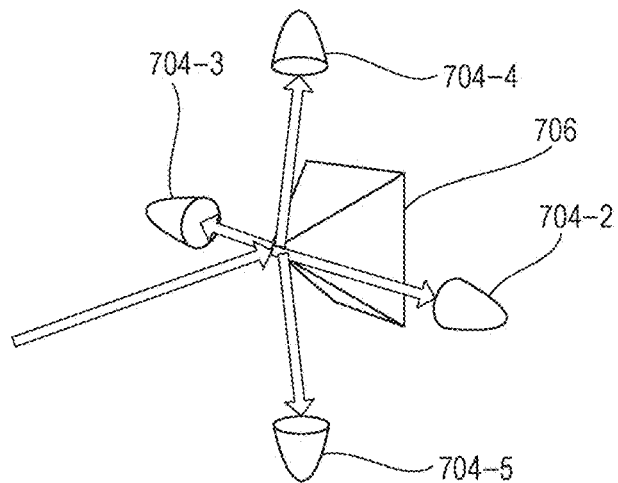
[Fig. 10A]
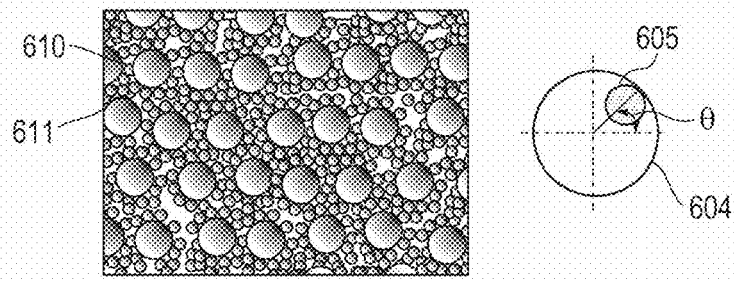
[Fig. 10B]
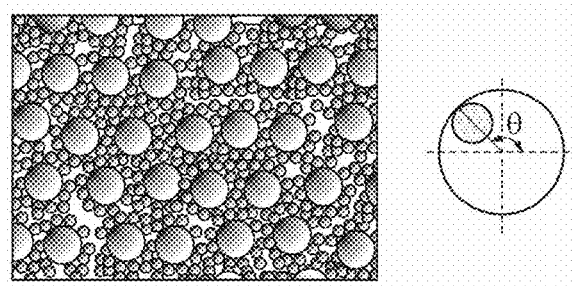
[Fig. 10C]
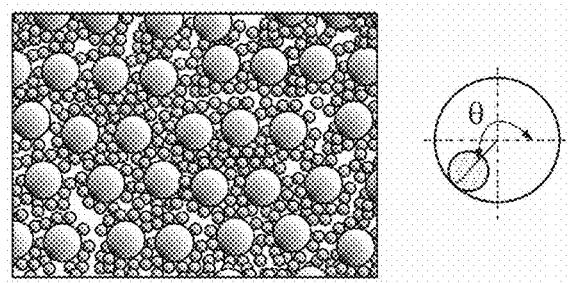

[Fig. 10D]
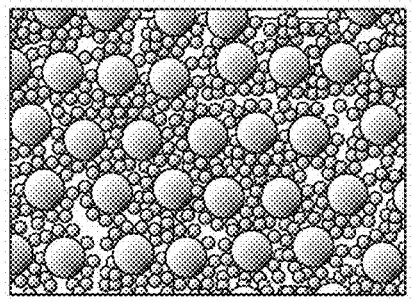
[Fig. 11]
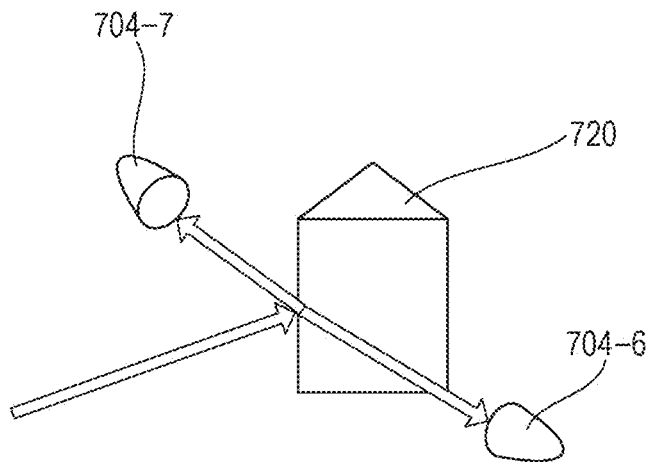
[Fig. 12]
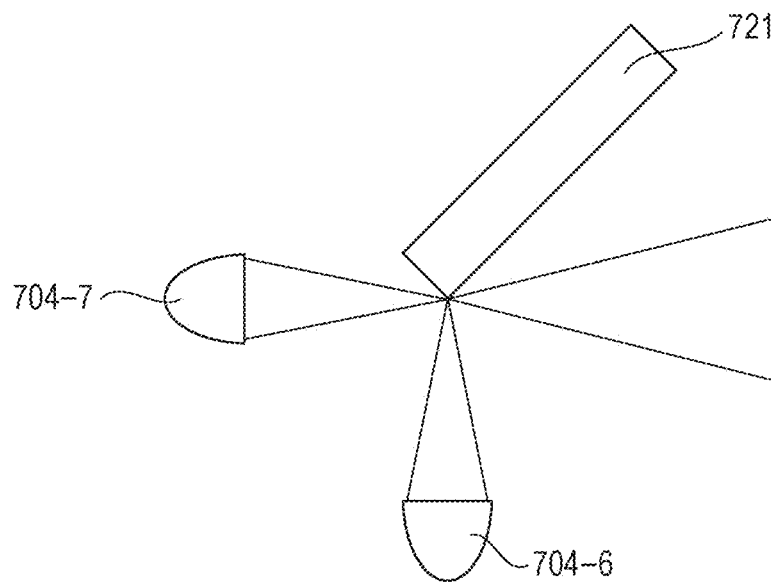

[Fig. 13A]
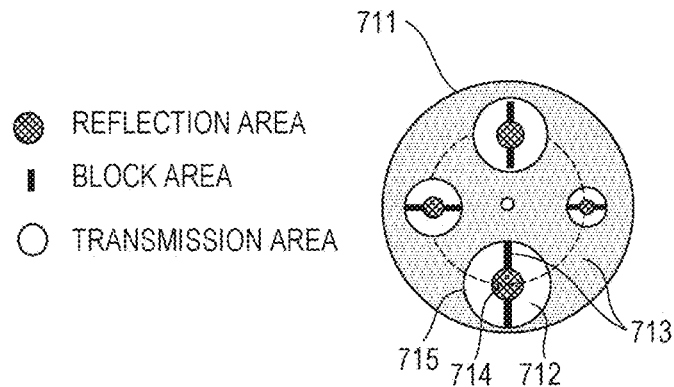
[Fig. 13B]
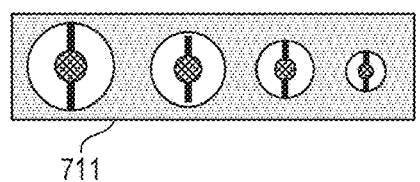
[Fig. 14A]
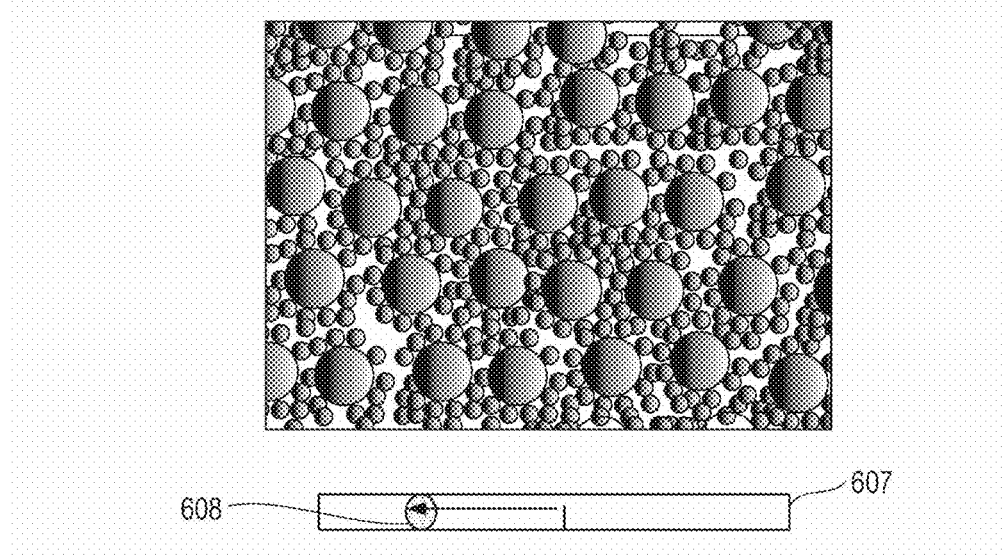

[Fig. 14B]
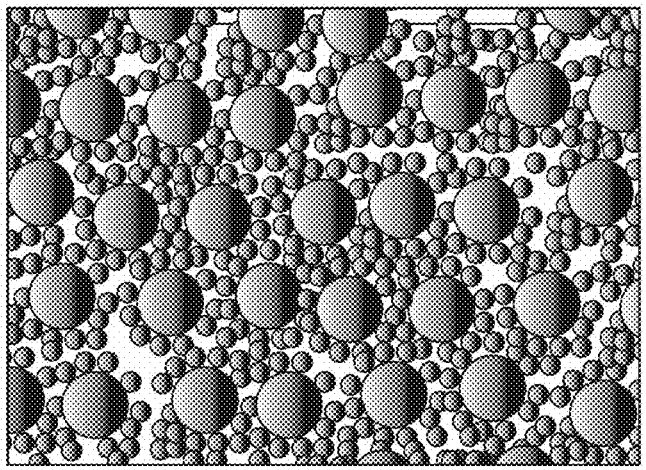
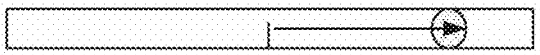

OPTICAL IMAGING APPARATUS AND METHOD FOR CONTROLLING THE SAME

TECHNICAL FIELD

The present invention relates to an optical imaging apparatus and a method for controlling the same, and in particular, relates to an optical imaging apparatus that is used for ophthalmic diagnosis and treatment and a method for controlling the same.

BACKGROUND ART

Eye examinations are widely performed for the purpose of early diagnosis and treatment of lifestyle-related diseases and diseases which are the leading causes of blindness. Ophthalmic equipment used for eye examinations includes a scanning laser ophthalmoscope (SLO), serving as an ophthalmic apparatus based on the principle of a confocal laser scanning microscope. The scanning laser ophthalmoscope is an apparatus (hereinafter, referred to as an "SLO apparatus") that scans a laser beam, serving as measurement light, over a fundus in a raster pattern and quickly obtains a high resolution planar image based on the intensity of return light associated with the measurement light.

It has recently been possible to acquire a higher resolution planar image of a fundus by increasing the beam diameter of measurement light in the SLO apparatus and significantly reducing the size of a spot of the measurement light on the fundus. In acquiring a planar image of the fundus, however, the signal-to-noise (S/N) ratio and resolution of the planar image are reduced due to aberrations of measurement light and its associated return light caused in an eye to be examined by an increase in beam diameter of the measurement light.

The reduction of the S/N ratio and the resolution is countered by measuring the aberrations of the measurement light and the return light caused in the eye to be examined in real time using a wavefront sensor and correcting the aberrations in the eye to be examined using a wavefront compensation device. An adaptive optics SLO apparatus (hereinafter, referred to as an "AOSLO apparatus") including an adaptive optics system, such as a wavefront compensation device, has been developed to enable acquisition of high resolution planar images.

To acquire a high resolution planar image, the beam diameter of measurement light is increased in the above-described confocal optical system. In some cases, the confocal optical system is allowed to include a non-confocal optical system depending on a region or tissue of a fundus, whose image is intended to be acquired, in order to increase the S/N ratio of a planar image.

NPL 1 describes an AOSLO apparatus having a configuration for increasing the S/N ratio of a planar image (blood vessel image) to be acquired. Specifically, return light from a fundus is split into two beams on an imaging plane of the return light and the beams are allowed to enter different optical sensors such that the sensors detect the beams. Signals from the optical sensors are subjected to calculation (subtraction) to form an image of a retina.

PTL 1 describes a configuration for forming an image of a very small biological substance. Specifically. PTL 1 describes that the shape of a pinhole in an optical sensor for receiving return light from a fundus is changed in order to acquire high resolution planar images of various regions and tissues of the fundus.

CITATION LIST

Patent Literature

PTL 1: Japanese Patent Laid-Open No. 2009-95632

Non Patent Literature

NPL 1: Sulai et al., "Visualization of retinal vascular structure and perfusion with a nonconfocal adaptive optics scanning light ophthalmoscope". J. Opt. Soc. Am. A, Vol. 31, No. 3, pp. 569-579, 2014

SUMMARY OF INVENTION

Technical Problem

The above-described AOSLO apparatus including the adaptive optics system can acquire a high resolution and high S/N ratio planar image.

In the configuration described in NPL 1, however, the two optical sensors for receiving return light from a fundus provide only information about a one-dimensional (for example, transverse) difference. Disadvantageously, a variation in a longitudinal direction cannot be enhanced. For example, the edge of a blood vessel extending transversely cannot be enhanced. The configuration leaves room for improvement.

The configuration described in PTL 1 does not include a return light splitting mechanism like that described in NPL 1. This configuration leaves room for improvement in functionality.

The present invention has been made in consideration of the above-described problem. The present invention provides an apparatus capable of capturing a high resolution and high S/N ratio planar image of a fundus to extract an image having an edge enhanced in an intended direction.

Solution to Problem

The present invention provides an optical imaging apparatus including a splitting unit configured to split return light, obtained by applying measurement light from a light source to an object to be examined via a measurement optical path, into a plurality of beams, a light receiving unit configured to measure intensities of the beams, a changing unit configured to change a ratio of signal components of an image to be generated based on the intensities of the beams, and a generating unit configured to generate an image by calculation using the changed ratio of the signal components.

Further features of the present invention will become apparent from the following description of exemplary embodiments with reference to the attached drawings.

BRIEF DESCRIPTION OF DRAWINGS

FIG. 1A is a diagram illustrating an exemplary appearance configuration of an AOSLO apparatus according to a first embodiment.

FIG. 1B is a diagram illustrating the appearance configuration of the AOSLO apparatus according to the first embodiment.

FIG. 2A is a diagram illustrating an exemplary configuration of an optical system of the AOSLO apparatus according to the first embodiment.

FIG. 2B is a diagram illustrating the configuration of the optical system of the AOSLO apparatus according to the first embodiment.

FIG. 3 is a graph illustrating a wavelength distribution of measurement light in the AOSLO apparatus according to the first embodiment.

FIG. 4 is a flowchart illustrating an image capture process in the first embodiment.

FIG. 5 is a diagram illustrating an exemplary configuration of a control software screen in the first embodiment.

FIG. 6 is a diagram illustrating an exemplary configuration of an image viewing software screen in the first embodiment.

FIG. 7A is a diagram illustrating an exemplary configuration of a splitting unit in the first embodiment.

FIG. 7B is a diagram illustrating another exemplary configuration of the splitting unit in the first embodiment.

FIG. 8 is a diagram illustrating an exemplary configuration of a light receiving unit in the first embodiment.

FIG. 9 is a diagram illustrating the configuration of the light receiving unit in the first embodiment.

FIG. 10A is a diagram illustrating an example of a displayed image in the first embodiment.

FIG. 10B is a diagram illustrating an example of a displayed image in the first embodiment.

FIG. 10C is a diagram illustrating an example of a displayed image in the first embodiment.

FIG. 10D is a diagram illustrating an example of a displayed image in the first embodiment.

FIG. 11 is a diagram illustrating an exemplary configuration of a light receiving unit in a second embodiment.

FIG. 12 is a diagram illustrating another exemplary configuration of the light receiving unit in the second embodiment.

FIG. 13A is a diagram illustrating an exemplary configuration of a splitting unit in the second embodiment.

FIG. 13B is a diagram illustrating another exemplary configuration of the splitting unit in the second embodiment.

FIG. 14A is a diagram illustrating an example of a displayed image in the second embodiment.

FIG. 14B is a diagram illustrating an example of a displayed image in the second embodiment.

DESCRIPTION OF EMBODIMENTS

Embodiments will be described in detail below. The following embodiments are not intended to restrict the present invention described in the appended claims. All of the combinations of features described in the embodiments are not necessary for solving problems in accordance with an embodiment of the present invention.

First Embodiment

A first embodiment of the present invention will be described.

In the first embodiment, an AOSLO apparatus, serving as an optical imaging apparatus, to which the present invention is applied will be described. The AOSLO apparatus includes an adaptive optics system and is an apparatus for capturing a high resolution planar image (AOSLO image) of a fundus. The AOSLO apparatus further includes a wide field scanning laser ophthalmoscope (WFSLO) unit for capturing a wide field angle planar image (WFSLO image) to assist acquisition of an AOSLO image, an anterior eye segment observation unit for determining the position of entrance of measurement light, and a fixation lamp unit for directing a line of sight to adjust an image capture region.

The AOSLO apparatus according to the present embodiment corrects optical aberrations of return light caused in an eye to be examined, serving as an object to be examined, by using a spatial light modulator to acquire a planar image. A good planar image of a fundus can be acquired irrespective of the eyesight of the eye to be examined or optical aberrations of the return light caused in the eye to be examined.

Although the apparatus includes the adaptive optics system in order to capture a high resolution planar image, the adaptive optics system may be omitted if the apparatus includes an optical system capable of achieving high resolution.

Appearance Configuration of AOSLO Apparatus

An exemplary appearance configuration of an AOSLO apparatus 101 according to the present embodiment will now be described with reference to FIGS. 1A and 1B. FIG. 1A is a top view of the AOSLO apparatus 101 and FIG. 1B is a side view thereof.

The AOSLO apparatus 101 includes a head unit 102 including an optical system, a stage unit 103 that moves the head unit 102 in horizontal and vertical directions, a face rest unit 104 that adjusts the position of a subject's face placed thereon, a liquid crystal display (LCD) monitor 105 that displays an operation screen or the like, and a control personal computer (PC) 106 that controls the entirety of the AOSLO apparatus 101.

The head unit 102 disposed on the stage unit 103 can be moved horizontally (in a direction along the page of FIG. 1A) by tilting a joystick 107 and can be moved vertically (in a direction perpendicular to the page of FIG. 1A) by rotating the joystick 107. The face rest unit 104 includes a chin rest 108 to support a chin and a chin rest actuator 109 including an electric stage to move the chin rest 108.

Configuration of Optical System

The optical system included in the head unit 102 will now be described with reference to FIGS. 2A and 2B.

Light emitted from a light source 201-1 is split into reference light 205 and measurement light 206-1 by an optical coupler 231. The measurement light 206-1 is applied to a subject's eye 207, serving as an object to be examined or an observation target, via a single-mode fiber 230-4, a spatial light modulator 259, an XY scanner unit 219-1, and a dichroic mirror 270-1, for example. A light flux 257 emitted from a fixation lamp 256 plays a role in prompting fixation or rotation of the subject's eye 207.

The measurement light 206-1 is reflected and scattered by the subject's eye 207, thus producing return light 208. The return light 208 travels backward along a measurement optical path and is then reflected by a beam splitter 258-3, so that the light enters a light receiving unit 700. The light receiving unit 700 includes detectors 704-1 to 704-5 (refer to FIGS. 8 and 9), each of which converts the intensity of light of the return light 208 into a voltage signal and outputs the signal. A planar image of a fundus of the subject's eye 207 is generated based on the signals output from the detectors 704-1 to 704-5. Although the entire optical system is configured as a dioptric system including lenses in the present embodiment, the optical system may be configured as a catoptric system including spherical mirrors instead of lenses.

Although the spatial light modulator of a reflective type is used as an aberration correction device, a transmissive spatial light modulator or a deformable mirror may be used.

Light Source of AOSLO Unit

The light source 201-1 and its surroundings will now be described. The light source 201-1, which is used as a light source for an AOSLO unit, is a super luminescent diode (SLD) light source, serving as a typical low coherent light source. The light source 201-1 emits light having an 840 nm wavelength and a 50 nm bandwidth. The low coherent light source is selected in order to acquire a planar image with little speckle noise. Although the SLD light source is selected, any other light source capable of emitting low coherent light may be used. For example, an amplified spontaneous emission (ASE) light source can be used.

As regards the wavelength, near-infrared light is suitable for measurement on an eye. Furthermore, a wavelength as short as possible can be used because the wavelength affects a resolution in a transverse direction of a planar image to be acquired. In this case, the wavelength is 840 nm. Any other wavelength may be selected depending on a measurement target region in an observation target.

Light emitted from the light source 201-1 passes through the single-mode fiber 230-1 and the optical coupler 231, where the light is split into the reference light 205 and the measurement light 206-1 at a ratio of 90:10. Polarizing controllers 253-2 and 253-4 are arranged near the optical coupler 231.

Reference Optical Path of AOSLO Unit

A reference optical path for the reference light 205 will now be described.

The reference light 205 obtained by the optical coupler 231 passes through an optical fiber 230-2 and then enters a light intensity measuring device 264. The light intensity measuring device 264, which measures the intensity of the reference light 205, is used to monitor the intensity of the measurement light 206-1.

Measurement Optical Path of AOSLO Unit

The measurement optical path for the measurement light 206-1 will now be described.

The measurement light 206-1 obtained by the optical coupler 231 is guided through the single-mode fiber 230-4 to a lens 235-1, where the light is adjusted to parallel light having a beam diameter of 4 mm.

The measurement light 206-1 passes through the beam splitter 258-3, a beam splitter 258-1, a lens 235-5, and a lens 235-6, and is then applied to the spatial light modulator 259.

The spatial light modulator 259 is controlled by the control PC 106 through a spatial light modulator driver 288 included in a driver unit 281.

The measurement light 206-1 is modulated by the spatial light modulator 259. After that, the light passes through a lens 235-7 and a lens 235-8 and is then applied to mirrors of the XY scanner unit 219-1. For the sake of simplification, the XY scanner unit 219-1 is illustrated as a single mirror in FIG. 2A. Actually, two mirrors, serving as an X scanner and a Y scanner, are arranged close to each other and are used to scan the measurement light 206-1 in a direction perpendicular to the optical axis over a retina 227 in a raster pattern. The mirrors of the XY scanner unit 219-1 are adjusted such that the optical axis of the measurement light 206-1 coincides with the axis of rotation of each of the mirrors of the XY scanner unit 219-1.

The X scanner, which scans the measurement light 206-1 in a direction along the page of FIG. 2A, is a resonant scanner. The resonant scanner is driven at a driving frequency of approximately 7.9 kHz. The Y scanner, which scans the measurement light 206-1 in a direction perpendicular to the page of FIG. 2A, is a galvanometer scanner. The galvanometer scanner is driven with a sawtooth waveform signal having a frequency of 32 Hz and a duty ratio of 84%. The driving frequency for the Y scanner is an important parameter that determines the frame rate of AOSLO image capture.

The XY scanner unit 219-1 is controlled by the control PC 106 through an optical scanner driver 282 included in the driver unit 281.

A lens 235-9 and a lens 235-10, which are included in an optical system for scanning the measurement light 206-1 over the retina 227, play a role in scanning the measurement light 206-1 over the retina 227 such that the fulcrum of the light coincides with the center of a pupil of the subject's eye 207.

Although the measurement light 206-1 has a beam diameter of 4 mm, the beam diameter may be increased to acquire a higher resolution optical image.

An electric stage 217-1 is movable in a direction indicated by arrows in FIG. 2A, so that the position of the lens 235-10 attached to the electric stage 217-1 can be moved to adjust a focus position.

The electric stage 217-1 is controlled by the control PC 106 through an electric stage driver 283 included in the driver unit 281.

Adjusting the position of the lens 235-10 brings the measurement light 206-1 into focus in a predetermined layer of the retina 227 of the subject's eye 207, so that the retina 227 can be observed and imaged. If the subject's eye 207 has ametropia or refractive errors, the subject's eye 207 can be observed and imaged in the above-described manner.

After entering the subject's eye 207, the measurement light 206-1 is reflected and scattered by the retina 227, thus producing the return light 208, which enters the light receiving unit 700. As will be described in detail later, the return light 208 entered the light receiving unit 700 is split into beams by a splitting unit and the beams are applied to the detectors 704-1 to 704-5. As regards the detectors 704-1 to 704-5, for example, avalanche photo diodes (APDs) or photomultiplier tubes (PMTs), which are high-speed, high-sensitive optical sensors, can be used.

Light Receiving Unit

An exemplary configuration of the light receiving unit 700 will now be described with reference to FIGS. 7A to 9.

After entering the light receiving unit 700, the return light 208 is partly reflected by central part of a splitting unit 711 disposed on an imaging plane defined by a lens, so that the reflected light is applied to the detector 704-1. The light except the light reflected by the splitting unit 711 partly passes through the splitting unit 711. After that, the light is split into four beams by a pyramid prism 706 disposed on an imaging plane defined by a lens. The four beams are applied to the detectors 704-2, 704-3, 704-4, and 704-5 (refer to FIG. 9).

FIG. 7A illustrates the splitting unit 711. As illustrated in FIG. 7A, the splitting unit 711 has a plurality of patterns 715 each including a reflection area 714 in its central part, a transmission area 712 surrounding the reflection area 714, and a block area 713 for blocking light such that the reflection area 714 is surrounded by the transmission area 712 and the block area 713. The splitting unit 711 is rotated and one of the patterns is selected and disposed such that the center of the selected pattern coincides with the optical axis of the return light 208.

Light 708 reflected by the reflection area 714 in the central part of the pattern 715 of the splitting unit 711 enters the detector 704-1. Light 709 passing through the transmission area 712 of the pattern 715 is split into four beams by the pyramid prism 706 disposed in the imaging plane. The four beams enter the respective detectors 704-2, 704-3, 704-4, and 704-5. The detectors 704-2 and 704-3 are arranged in a direction identical to a scanning direction of an X scanner included in an XY scanner unit 219-2. The detectors 704-4 and 704-5 are arranged in a direction identical to a scanning direction of a Y scanner included in the XY scanner unit 219-2.

The splitting unit 711 has an oval pattern that appears in the form of a circle when viewed in a direction along the optical axis of the return light 208 while the oval pattern is being selected in an arrangement in which the splitting unit 711 is placed at an angle to the optical axis of the return light 208. For the convenience of illustration, each pattern is illustrated in the form of a circle. The splitting unit 711 is controlled by the control PC 106 through a pattern selection controller 289 in such a manner that one of the patterns is selected.

When a pattern having a small-diameter reflection area 714 in its central part is selected, a confocal image (AOSLO image) generated based on an output of the detector 704-1 has a higher resolution in the optical axis direction but has a narrower depth of focus. Increasing the diameter of the reflection area 714 in the central part reduces the resolution in the optical axis direction but increases the depth of focus. As regards non-confocal images generated based on outputs of the detectors 704-2 to 704-5, when a pattern having a small-diameter reflection area 714 and a large transmission area 712 surrounding the reflection area 714 is selected, a signal intensity detected by each detector increases, resulting in an increase in the S/N ratio of a differential image (non-confocal image) to be generated. When a pattern having a large-diameter reflection area 714 in its central part and a small transmission area 712 surrounding the reflection area 714 is selected, the signal intensity decreases, resulting in a reduction in the S/N ratio.

Accordingly, selecting a pattern suitable for an observation image enables adjustment for proper resolution and a proper S/N ratio of an image to be captured. Alternatively, the splitting unit 711 is configured such that a plate having a plurality of patterns arranged in a circle as illustrated in FIG. 7A is mechanically rotatable to select a pattern. The splitting unit 711 may be configured such that a plate having a plurality of patterns arranged in a line as illustrated in FIG. 7B is mechanically slidable to select a pattern. The light receiving unit 700 may include any other suitable mechanism for splitting return light.

Voltage signals obtained by the detectors 704-1 to 704-5 are converted into digital values by an analog-to-digital (AD) board 276-1 in the control PC 106. The digital values are input to the control PC 106.

Let Ia, Ib, Ic, and Id denote the digital values of the voltage signals obtained from light applied to the detectors 704-2, 704-3, 704-4, and 704-5 at a certain time point. A derivative Iab, serving as a signal component in the X direction, and a derivative Icd, serving as a signal component in the Y direction, are calculated by Expressions (1) and (2).

$$Iab = (Ia - Ib)/(Ia + Ib) \quad (1)$$

$$Icd = (Ic - Id)/(Ic + Id) \quad (2)$$

An edge-enhanced image can be acquired by using an image generated based on the derivatives Iab and Icd, serving as the signal components in the X and Y directions.

In the above-described configuration, the light receiving unit includes the four detectors for generating a non-confocal image, thus obtaining the values Ia, Ib, Ic, and Id. The light receiving unit 700 may have another configuration such that two detectors are arranged symmetrically with respect to a line passing through a splitting point of the pyramid prism and the detectors are rotated about the optical axis of the light 709 relative to the pyramid prism in order to obtain the value Iab and information about a rotation angle θ.

Entirety of WFSLO Unit

A WFSLO unit will now be described with reference to FIG. 2A. The WFSLO unit has fundamentally the same configuration as that of the AOSLO unit. A description of the previously described components is accordingly omitted.

Light emitted from a light source 201-2 is applied to the subject's eye 207 via a lens 235-2, lenses 235-11 to 235-14, the XY scanner unit 219-2, the dichroic mirror 270-1, and dichroic mirrors 270-2 and 270-3, for example. The light source 201-2 is an SLD light source similar to that for the AOSLO unit. The light source 201-2 emits light having a 920 nm wavelength and a 20 nm bandwidth.

Measurement Optical Path of WFSLO Unit

A measurement optical path for measurement light 206-2 will now be described. The measurement light 206-2 emitted from the light source 201-2 is applied to the subject's eye 207 via the lens 235-2, the lenses 235-11 to 235-14, the XY scanner unit 219-2, the dichroic mirror 270-1, and the like.

The X scanner, serving as a component of the XY scanner unit 219-2, for scanning the measurement light 206-2 in the direction along the page of FIG. 2A is a resonant scanner, which is driven at a driving frequency of approximately 3.9 kHz. The Y scanner for scanning the measurement light 206-2 in the direction perpendicular to the page of FIG. 2A is a galvanometer scanner, which is driven with a sawtooth waveform signal having a frequency of 15 Hz and a duty ratio of 84%. The driving frequency for the Y scanner is an important parameter that determines the frame rate of a WFSLO image.

Although the measurement light 206-2 has a beam diameter of 1 mm, the beam diameter may be increased to acquire a higher resolution optical image.

After entering the subject's eye 207, the measurement light 206-2 is reflected and scattered by the retina 227, thus producing return light 208'. The return light 208' enters a detector 238-2 via the dichroic mirrors 270-1 to 270-3, the lenses 235-13 and 235-14, the lens 235-2, lenses 235-3 and 235-4, the XY scanner unit 219-2, and a beam splitter 258-2. The control PC 106 generates a WFSLO image based on a voltage signal of the return light 208' detected by the detector 238-2.

Beacon Unit

A beacon unit for measuring aberrations caused in the subject's eye 207 will now be described.

Measurement light 206-3 emitted from a light source 201-3 is applied to the subject's eye 207 via lenses 235-15 and 235-16, a dichroic mirror 270-4, and the like.

The measurement light 206-3 is allowed to enter the subject's eye 207 so as to be offset from the center of a cornea 226 of the subject's eye 207 in order to avoid reflection by the cornea 226. Return light 208" associated with the measurement light 206-3 partly enters a wavefront sensor 255 via the dichroic mirror 258-1 and a pinhole 298. In the wavefront sensor 255, aberrations of the return light 208" caused in the subject's eye 207 are measured. The pinhole 298 is disposed to block unnecessary light other than the return light 208". The wavefront sensor 255 is electrically connected to the control PC 106. The wavefront sensor 255, which is a Shack-Hartmann wavefront sensor, has a measurement range of −10D to +5D. Information about the aberrations obtained by the wavefront sensor 255 is expressed using Zernike polynomials by the control PC 106. The information indicates the aberrations caused in the subject's eye 207. Zernike polynomials include tilt terms, a defocus term, astigmatism terms, coma terms, and trefoil terms. The light source 201-3 emits light having a center wavelength of 760 nm and a bandwidth of 20 nm.

The lenses 235-5 to 235-10 are arranged such that the cornea 226, the XY scanner unit 219-1, the wavefront sensor 255, and the spatial light modulator 259 are optically conjugate to one another. Consequently, the wavefront sensor 255 can measure aberrations of the return light caused in the subject's eye 207. The spatial light modulator 259 can correct the aberrations of the return light caused in the subject's eye 207.

Fixation Lamp Unit

A fixation lamp unit will now be described. The fixation lamp 256, which includes a light emitting display module, has a display surface (27 by 27 mm, 128 by 128 pixels) on an XY plane. As the fixation lamp 256, a liquid crystal display, an organic electroluminescent (EL) display, or a light emitting diode (LED) array can be used. The subject's eye 207 looks fixedly at the light flux 257 from the fixation lamp 256, so that fixation or rotation of the subject's eye 207 is promoted. In the display surface of the fixation lamp 256, a blinking cross pattern is displayed at any lighting position 265, for example, as illustrated in FIG. 2B.

The light flux 257 from the fixation lamp 256 is applied to the retina 227 via lenses 235-17 and 235-18 and the dichroic mirrors 270-1 to 270-3. The lenses 235-17 and 235-18 are arranged such that the display surface of the fixation lamp 256 and the retina 227 are optically conjugate to each other. The fixation lamp 256 is controlled by the control PC 106 through a fixation lamp driver 284 in the driver unit 281.

Anterior Eye Segment Observation Unit

An anterior eye segment observation unit will now be described.

Light emitted from an anterior eye segment illumination light source 201-4 is applied to the subject's eye 207. Reflected light associated with the light enters a charge coupled device (CCD) camera 260 via the dichroic mirrors 270-1, 270-2, and 270-4 and lenses 235-19 and 235-20. The light source 201-4 is an LED emitting light having a center wavelength of 740 nm.

Focus, Shutter, and Astigmatism Correction

As described above, the optical system included in the head unit 102 includes the AOSLO unit, the WFSLO unit, the beacon unit, the fixation lamp unit, and the anterior eye segment observation unit. The AOSLO unit includes the electric stage 217-1, and the WFSLO unit, the beacon unit, and the fixation lamp unit include electric stages 217-2, 217-3, and 217-4, respectively. Moving the four electric stages operatively associated with one another adjust focus positions. The focus positions can be individually adjusted by individually moving the electric stages.

In addition, the AOSLO unit, the WFSLO unit, and the beacon unit each include a shutter (not illustrated). Whether to permit measurement light to enter the subject's eye 207 can be individually controlled by opening or closing the shutter. Although the shutter is used in this case, this control can be achieved by directly turning on or off the light sources 201-1 to 201-3. Similarly, the control in the anterior eye segment observation unit and the fixation lamp unit can be achieved by turning on or off the light source 201-4 and the fixation lamp 256.

The lens 235-10 is replaceable. A spherical lens or a cylindrical lens can be used depending on aberrations (refractive errors) in the subject's eye 207. The lens 235-10 is not limited to one lens. A plurality of lenses can be arranged in combination.

Wavelengths

FIG. 3 illustrates a distribution of wavelengths of the light sources for the AOSLO unit, the WFSLO unit, the beacon unit, the fixation lamp unit, and the anterior eye segment observation unit. The light sources have different wavelength ranges for separation of light with the dichroic mirrors 270-1 to 270-4. FIG. 3, which illustrates the differences in wavelength among the light sources, is not intended to define light intensities and their spectral shapes associated with the light sources.

Image Formation

Formation of a captured image will now be described.

Beams applied to the detectors 704-1 to 704-5 are converted into voltage signals based on the intensities of the beams. The voltage signals obtained by the detectors 704-1 to 704-5 are converted into digital values in the AD board 276-1 in the control PC 106. The control PC 106 performs data processing in synchronization with an operation or driving frequency of the XY scanner unit 219-1, thus generating an AOSLO image (a confocal image and a non-confocal image). A data acquisition rate of the AD board 276-1 is 15 MHz. Similarly, a voltage signal obtained by the detector 238-2 is converted into a digital value in an AD board 276-2 in the control PC 106. A WFSLO image is formed based on the digital value.

Control Software Screen

A control software screen displayed on the LCD monitor 105 will now be described with reference to FIG. 5. In FIG. 5, the control software screen includes an execution button 501 to start image capture, a stop button 502 to terminate processing, an electric stage button 503 to finely adjust the chin rest, a focus adjustment button 504 to adjust focus, a WFSLO image capture button 505 to start WFSLO image capture, an aberration measurement button 506 to start measurement of aberrations, an AOSLO image capture button 507 to start AOSLO image capture, an aberration correction display area 511 for displaying values of aberration amounts, an anterior eye segment display area 512 for displaying an image of an anterior eye segment, a fixation lamp position display area 513 for specifying the lighting position 265 on the fixation lamp 256, a wavefront sensor display area 514 for displaying a Hartmann image detected by the wavefront sensor 255, a WFSLO display area 515 for displaying a WFSLO image, a WFSLO intensity display area 516 for displaying the intensity of an output signal of the detector 238-2, a WFSLO recording button 517 to record a WFSLO image, an AOSLO display area 518 for displaying an AOSLO image, an AOSLO intensity display area 519 for displaying the intensity of an output signal from the detector 704-1, an AOSLO recording button 520 to record an AOSLO image, an autofocus button 521 for automatic focusing, an aberration correction button 522 to start aberration correction, an image capture condition setting button 523 to change a set image capture condition, a depth adjustment button 524 to adjust the depth of an AOSLO image to be captured, and an edge enhancement mode button 606 to provide an edge enhancement mode of a non-confocal image.

Image Viewing Software Screen

An image viewing software screen displayed on the LCD monitor 105 will now be described with reference to FIG. 6.

In FIG. 6, the image viewing software screen includes a confocal image display area 601 for displaying a confocal image, an image number selection area 602 to select an image to be processed, an image quality control 603 to control the quality of a confocal image displayed and the quality of a non-confocal image displayed, a control range 604, associated with an angle control 605, for control of an angle at which an edge is to be enhanced, the angle control 605 to change an angle at which an edge is to be enhanced, the edge enhancement mode button 606 to provide the edge enhancement mode, a non-confocal image display area 611 for displaying a non-confocal image, and a focus depth control 612 to change the pattern in the splitting unit 711.

Image Capture Process

An image capture process performed by the AOSLO apparatus according to the present embodiment will now be described with reference to FIGS. 4 and 5.

FIG. 4 illustrates the image capture process. Steps included in the process will be described below. The process is performed under the control of the control PC 106 unless otherwise stated.

Step 1: Start Up Apparatus and Check Various Conditions

When an operator turns on the control PC 106 and the AOSLO apparatus, measurement control software is started in the apparatus, so that the control software screen illustrated in FIG. 5 is displayed on the LCD monitor 105. In this state, a subject is allowed to set his or her face on the face rest unit 104.

Step 2: Capture Image of Anterior Eye Segment

When the operator presses the execution button 501 on the control software screen, an image of an anterior eye segment captured by the CCD camera 260 is displayed in the anterior eye segment display area 512. If the center of a pupil displayed is not in a substantially correct state, namely, the center of the pupil is not displayed at the middle of the anterior eye segment display area 512, the operator moves the head unit 102 to a substantially correct position by using the joystick 107. If further adjustment is needed, the operator presses the electric stage button 503 on the control software screen to slightly move the chin rest actuator 109.

Step 3: Capture WFSLO Image

If the image of the anterior eye segment is displayed in substantially the correct state, a WFSLO image captured by the detector 238-2 is displayed in the WFSLO display area 515. The lighting position 265 on the fixation lamp 256 is set at a middle position in the fixation lamp position display area 513 to direct the line of sight of the subject's eye 207 to the middle of the fixation lamp 256.

Next, the operator orders adjustment by using the focus adjustment button 504 while viewing the WFSLO intensity display area 516. The operator orders adjustment such that the signal intensity displayed in the WFSLO intensity display area 516 increases. A signal intensity detected by the detector 238-2 in the WFSLO unit is displayed in a time series graph showing signal intensity plotted against time in the WFSLO intensity display area 516. In response to ordering adjustment with the focus adjustment button 504, the lenses 235-10, 235-14, 235-16, and 235-18 are moved simultaneously, thus adjusting the focus positions.

The operator checks that the WFSLO image is clearly displayed in the WFSLO display area 515 and then presses the WFSLO recording button 517. In response to pressing the WFSLO recording button 517. WFSLO data is stored to a storage unit (not illustrated).

Step 4: Determine AOSLO Image Capture Position

After checking the WFSLO image displayed in the WFSLO display area 515, the operator determines an AOSLO image capture position, at which the operator intends to capture an AOSLO image, by using a method which will be described hereinafter. The operator directs the line of sight of the subject's eye 207 by using the fixation lamp 256 so that this position is located at the middle of the WFSLO display area 515.

There are two methods for determining an AOSLO image capture position. According to one of the methods, the operator specifies the lighting position 265 on the fixation lamp 256 in the fixation lamp position display area 513. The cross pattern on the fixation lamp 256 is turned on at the specified position. According to the other one of the methods, the operator specifies an intended position in the WFSLO display area 515. Each of pixels of the WFSLO display area 515 is associated with corresponding one of positions on the fixation lamp 256 and data indicating the association is stored. The lighting position 265 on the fixation lamp is automatically shifted to a specified position, thus directing the line of sight to the intended position.

The process proceeds to the next step in response to an instruction from the operator who has checked that the AOSLO image capture position was shifted to the middle of the WFSLO display area 515.

Step 5: Aberration Correction

When the operator presses the aberration measurement button 506, the measurement light 206-2, serving as WFSLO measurement light, is interrupted and the shutter for beacon light emitted from the light source 201-3 is opened, so that the measurement light 206-3, serving as beacon light, is applied to the subject's eye 207. A Hartmann image detected by the wavefront sensor 255 is displayed in the wavefront sensor display area 514. Aberrations calculated from the Hartmann image are displayed in the aberration correction display area 511. The aberrations displayed are classified as a defocus component (in units of μm) and all aberration amounts (in units of μm RMS). Since the positions of the lenses 235-10 and 235-16, serving as focusing lenses for AOSLO measurement light and beacon light, have been adjusted in step 3, preparation for aberration measurement is complete in this step. Specifically, the return light 208" associated with the measurement light 206-3 is ready to pass through the pinhole 298 without being interrupted and reach the wavefront sensor 255.

In this state, when the autofocus button 521 is pressed, the positions of the lenses 235-10, 235-14, 235-16, and 235-18 are adjusted so that the value of the defocus component is reduced.

When the operator presses the aberration correction button 522, the spatial light modulator 259 is adjusted so that the aberration amounts are reduced. The aberration amounts are displayed as values in real time. When each aberration amount is less than or equal to a predetermined threshold value (0.03 μm RMS), the AOSLO image capture button 507 automatically enters a pressed state. Thus, the process proceeds to the next step. The threshold value for the aberration amounts can be set to any value. If each aberration amount is not less than or equal to the threshold value, the operator can press an aberration correction pause button 508 to stop aberration correction and then press the AOSLO image capture button 507 in order to allow the process to proceed to the next step.

Step 6: Capture AOSLO Image

When the operator presses the AOSLO image capture button 507, the measurement light 206-3, serving as beacon light, is interrupted and the shutter for the AOSLO measurement light 206-1 is opened, thus applying the measurement light 206-1 to the subject's eye 207. An AOSLO image subjected to aberration correction is displayed in the AOSLO display area 518. Furthermore, a signal intensity detected by the detector 704-1 in the AOSLO unit is displayed in a time series graph in the AOSLO intensity display area 519 in a manner similar to the WFSLO intensity display area 516.

If the signal intensity is insufficient, the operator orders adjustment in order to increase the signal intensity, namely, adjusts the focus positions and the chin rest position while viewing the AOSLO intensity display area 519.

Furthermore, the operator can specify an angle of view for image capture, a frame rate, and image capture time by using the image capture condition setting button 523.

Additionally, the operator controls the depth adjustment button 524 to move the lens 235-10, thus enabling adjustment of an image capture range in a depth direction of the subject's eye 207. Specifically, an image of an intended layer, e.g., a photoreceptor cell layer, a nerve fiber layer, or a retinal pigment epithelium layer, can be captured.

The operator checks that the AOSLO image is clearly displayed in the AOSLO display area 518 and then presses the AOSLO recording button 520. In response to pressing the AOSLO recording button 520, AOSLO data is stored to the storage unit. After that, the measurement light 206-1 is interrupted. If the operator intends to change the depth of focus of the AOSLO image, the operator may operate the focus depth control 612 to change the size of the reflection area of the pattern in the splitting unit 711, thus changing the pattern in the splitting unit 711 to another pattern. After that, an AOSLO image may be captured again.

Step 7: Display Edge-Enhanced AOSLO Image

In response to pressing the edge enhancement mode button 606 (refer to FIG. 5), switching from AOSLO image display to edge-enhanced image display is done. Specifically, switching from display of FIG. 5 to display of FIG. 6 is done.

When the operator rotates the angle control 605 in FIG. 6, an angle at which the AOSLO image is edge-enhanced is changed depending on the angle of rotation.

In response to pressing the edge enhancement mode button 606 (refer to FIG. 6), switching from the above-described display to normal AOSLO image display (or switching from display of FIG. 6 to display of FIG. 5) is done. If the operator intends to change the depth of focus of the edge-enhanced image, the operator may give an instruction to change the pattern in order to change the size of the transmission area of the pattern in the splitting unit 711. After that, the AOSLO image may be captured again.

Step 8: Select Next Operation

To change the image capture position, the process proceeds to step 4. To switch between right and left eyes, the process returns to step 2. To terminate the process, the process proceeds to step 9.

Step 9: Terminate Process

In response to pressing the stop button 502, the process is terminated.

Image Confirmation

A method for forming an image based on data capture by the AOSLO apparatus according to the present embodiment to confirm the image will now be described with reference to FIG. 6.

In response to an instruction from the operator, image viewing software for visualizing captured image data is started, thus displaying the image viewing software screen of FIG. 6 on the LCD monitor 105.

The stored WFSLO data or AOSLO data can be read and an image can be formed based on the read data.

The operator specifies an image to be display by, for example, entering an image number in the image number selection area 602. Image data items numbered in the order captured are stored in the storage unit. Image data assigned the specified image number is read from the storage unit and images based on the image data are simultaneously displayed in the confocal image display area 601 and the non-confocal image display area 611.

The image quality control 603 includes control tabs for controlling brightness, contrast, and gamma of images. Sliding each control tab to the right or the left can give an instruction to control the quality of the images displayed in the confocal image display area 601 and the non-confocal image display area 611.

An edge-enhanced image, generated based on signals from the detectors 704-2 to 704-5, of the fundus is displayed in the non-confocal image display area 611. As regards images displayed in the confocal image display area 601 and the non-confocal image display area 611, switching between a non-confocal image and a confocal image may be done by using the edge enhancement mode button 606.

The operator rotates the angle control 605 to adjust an angle at which the non-confocal image displayed in the non-confocal image display area 611 is edge-enhanced. The angle control 605 can regulate the shadow direction of the image by turning the angle control 605 along the circumference of the control range 604.

Values (x, y) depending on the rotation angle θ are obtained by Expression (3), the obtained values are multiplied by the derivatives Iab and Icd, serving as signal components in the X and Y directions, respectively, thus changing the ratio of the signal components. A value Iad obtained by changing the ratio is used to form an image to be displayed. Thus, the image subjected to shading depending on the angle indicated by the angle control 605 is displayed. The value Iad is obtained by calculation using Expression (4).

$$x = 1 \cos \theta$$
$$y = 1 \sin \theta \quad (3)$$

$$Iad = xIab + yIcd \quad (4)$$

As illustrated in FIGS. 10A to 10D, for example, an image 610 of photoreceptor cells of a fundus can be displayed based on the above-described value Iad calculated based on the rotation angle indicated by the angle control 605, and the orientation of shading of the image can be controlled.

As an angle-control interface instead of the angle control 605, a method of controlling the angle θ as a mechanical volume may be used. Alternatively, a method of determining, as the angle θ, an angle formed between a line connecting the middle of a displayed image and a selected point on the image and a horizontal line of the image may be used. Any other suitable method may be used.

As described above, the use of four signals from the detectors 704-2 to 704-5 enables display of an image with shading at any angle. Thus, a more flexible and detailed observation image can be obtained.

Second Embodiment

Edge enhancement (shading control) by the four detectors has been described in the first embodiment. A second embodiment will now be described with respect to edge enhancement (shading control) by two detectors.

The light receiving unit 700, illustrated in FIG. 9, is configured as illustrated in FIG. 11 such that light is split into two beams by a knife edge prism 720 in the form of a triangular prism and the beams are received by two photodetectors 704-6 and 704-7. As illustrated in FIG. 12, the light receiving unit 700 may be configured such that light is split into two beams by an edge of a mirror 721 and the two beams are received by the photodetectors 704-6 and 704-7.

In each of the above-described configurations, the splitting unit 711, illustrated in FIG. 7A or 7B, is configured as illustrated in FIG. 13A or 13B. The transmission area 712 includes two segments so that two beams obtained by splitting light enter the photodetectors 704-6 and 704-7.

In this case, Expression (1) for obtaining the intensity of a signal component is as described above. In Expression (2), Icd=0.

In this case, the image viewing software screen displayed on the monitor 105 includes a control 608, which is capable of adjusting a coefficient x in the following arithmetic expression in a slider control range 607, instead of the control range 604.

$$Icd = xIad (-1 \leq x \leq +1, x \neq 0) \quad \text{[Math. 1]}$$

The rate of shading in the X direction may be controlled as illustrated in FIGS. 14A and 14B by indicating control of the coefficient x with the control 608.

As described above, the configuration with the two detectors is simpler than the above-described configuration with the four detectors and can obtain features of an observation image that is more flexible and detailed than that obtained by a conventional configuration with no mechanism for edge enhancement control.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2014-145915, filed Jul. 16, 2014, and 2015-080445, filed Apr. 9, 2015 which are hereby incorporated by reference herein in their entirety.

The invention claimed is:

1. An optical imaging apparatus comprising:
   a splitting unit configured to split return light into a first beam and a second beam, the return light being obtained by applying measurement light from a light source to an object to be examined via a measurement optical path;
   a first and a second light receiving units configured to measure intensities of the first and second beams respectively;
   a changing unit configured to change a ratio of the intensity of the first beam and the intensity of the second beam;
   a calculation unit configured to obtain a value calculated with the changed ratio, the intensity of the first beam and the intensity of the second beam; and
   a generating unit configured to generate an image based on the calculated value,
   wherein the splitting unit includes a first splitting portion configured to extract a third beam of a central part of the return light and a second splitting portion configured to split a surround part surrounding the central part of the return light into the first beam and the second beam, and
   wherein the generating unit generates a confocal image based on the third beam.

2. The apparatus according to claim 1, further comprising:
   a specifying unit configured to specify an angle,
   wherein the changing unit changes the ratio of the intensity of the first beam and the intensity of the second beam in accordance with the specified angle.

3. The apparatus according to claim 1, further comprising:
   a specifying unit configured to specify a quantity of each of the first and the second beams.

4. The apparatus according to claim 1, wherein the second splitting portion splits the return light into the first beam, the second beam, a fourth beam and a fifth beam.

5. The apparatus according to claim 4, further comprising:
   a specifying unit configured to specify an angle,
   wherein the ratio of the intensities of the first, the second, the fourth and the fifth beams is changed in accordance with the specified angle, and
   wherein the calculation unit obtains the value calculated with the changed ratio and the intensities of the first, the second, the fourth and the fifth beams.

6. The apparatus according to claim 1, wherein the image generated by the generating unit is a non-confocal image of a fundus.

7. The apparatus according to claim 2, further comprising:
   a display unit configured to display the image generated by the generating unit,
   wherein the display unit displays the generated image together with an image for specifying the angle.

8. A method for controlling an optical imaging apparatus, the method comprising:
   a splitting step of splitting return light into a first beam and a second beam, the return light being obtained by applying measurement light from a light source to an object to be examined via a measurement optical path;
   a light receiving step of measuring intensities of the first and the second beams respectively;
   a changing step of changing a ratio of the intensity of the first beam and the intensity of the second beam;

a calculating step of obtaining a value calculated with the changed ratio, the intensity of the first beam and the intensity of the second beam; and a generating step of generating an image based on the calculated value, wherein the splitting step includes a first splitting step of extracting a third beam of a central part of the return light and a second splitting step of splitting a surround part surrounding the central part of the return light into the first beam and the second beam, and wherein the generating step generates a confocal image based on the third beam.

9. An optical imaging apparatus comprising:

a splitting unit configured to split return light into a first beam and a second beam, the return light being obtained by applying measurement light from a light source to an object to be examined, wherein the splitting unit includes a first splitting portion configured to extract a third beam of a central part of the return light and a second splitting portion configured to split a surrounding part that surrounds the central part of the return light into the first beam and the second beam;

first and second light receiving units configured to measure intensities of the first and second beams respectively;

a setting unit configured to set a direction for enhancement of an edge of an subject in an image;

a calculation unit configured to calculate a value based on a first intensity value measured by the first light receiving unit, a second intensity value measured by the second light receiving unit and the direction set by the setting unit; and a generating unit configured to generate the image based on a plurality of values calculated by the calculation unit, wherein the generating unit further generates a confocal image based on the third beam.

10. The apparatus according to claim 9, wherein the setting unit comprises a specifying unit configured to specify an angle, wherein the setting unit sets the direction in accordance with the specified angle.

11. The apparatus according to claim 9, further comprising:

a specifying unit configured to specify a quantity of each of the first and the second beams.

12. The apparatus according to claim 9, wherein the second splitting portion splits the return light into the first beam, the second beam, a fourth beam and a fifth beam.

13. The apparatus according to claim 12, further comprising:

a specifying unit configured to specify an angle, wherein the setting unit sets the direction in accordance with the specified angle, wherein the calculation unit obtains the value calculated with the set direction and the first intensity value of the first beam, the second intensity value of the second beam, an intensity value of the fourth beam, and an intensity value of the fifth beam.

14. The apparatus according to claim 9, wherein the image generated by the generating unit is a non-confocal image of a fundus.

15. The apparatus according to claim 10, further comprising:

a display unit configured to display the image generated by the generating unit, wherein the display unit displays the generated image together with an image for specifying the angle.

16. A method for controlling an optical imaging apparatus, the method comprising:

a splitting step of splitting return light into a first beam and a second beam, the return light being obtained by applying measurement light from a light source to an object to be examined, wherein the splitting step includes a first splitting step of extracting a third bean of a central part of the return light and a second splitting step of splitting a surrounding part that surrounds the central part of the return light into the first beam and the second beam;

a light receiving step of measuring intensities of the first and the second beams respectively;

a setting step of setting a direction for enhancement of an edge of an subject in an image;

a calculating step of calculating a value based on a first intensity value and a second intensity value measured in the light receiving step and the direction set in the setting step; and a generating step of generating the image based on a plurality of values calculated in the calculation step, wherein the generating step further generates a confocal image based on the third beam.

* * * * *